United States Patent
Yilmaz İnan et al.

(10) Patent No.: US 10,351,637 B2
(45) Date of Patent: Jul. 16, 2019

(54) FORMULATION AND LENS MANUFACTURING PROCESS FOR THE PRODUCTION OF INTRAOCULAR LENS (IOL)

(71) Applicant: TUBITAK, Ankara (TR)

(72) Inventors: Tülay Yilmaz İnan, Kocaeli (TR); Hacer Doğan, Kocaeli (TR); Nevin Bekīr, Kocaeli (TR); Zekai Korlu, Kocaeli (TR); Mustafa Candemīr, Kocaeli (TR)

(73) Assignee: TUBITAK, Ankara (TR)

( * ) Notice: Subject to any disclaimer, the term of this patent is extended or adjusted under 35 U.S.C. 154(b) by 181 days.

(21) Appl. No.: 15/307,370

(22) PCT Filed: May 7, 2015

(86) PCT No.: PCT/IB2015/053346
§ 371 (c)(1),
(2) Date: Oct. 28, 2016

(87) PCT Pub. No.: WO2015/170278
PCT Pub. Date: Nov. 12, 2015

(65) Prior Publication Data
US 2017/0044274 A1    Feb. 16, 2017

(30) Foreign Application Priority Data

May 7, 2014    (TR) ............... a 2014 05120

(51) Int. Cl.
*C08F 2/50* (2006.01)
*C08F 220/34* (2006.01)
*A61F 2/16* (2006.01)
*B29D 11/00* (2006.01)
*G02B 1/04* (2006.01)
*C08F 220/18* (2006.01)
*C08F 220/30* (2006.01)
*B29K 33/00* (2006.01)
*B29K 105/00* (2006.01)

(52) U.S. Cl.
CPC ............. *C08F 2/50* (2013.01); *A61F 2/16* (2013.01); *B29D 11/00009* (2013.01); *B29D 11/00442* (2013.01); *C08F 220/34* (2013.01); *G02B 1/041* (2013.01); *A61F 2002/16965* (2015.04); *B29K 2033/08* (2013.01); *B29K 2105/0002* (2013.01); *B29K 2105/0005* (2013.01); *B29K 2105/0044* (2013.01); *B29K 2909/08* (2013.01); *B29K 2995/0018* (2013.01); *B29K 2995/0093* (2013.01); *C08F 220/18* (2013.01); *C08F 220/30* (2013.01); *G02B 1/043* (2013.01)

(58) Field of Classification Search
CPC ........ C08F 2/50; C08F 220/34; C08F 220/18; C08F 220/30; B29D 11/00009; B29D 11/00442; G02B 1/041; G02B 1/043; A61F 2/16; A61F 2002/16965; B29K 2105/0044; B29K 2105/0005; B29K 2033/08; B29K 2909/08; B29K 2995/0018; B29K 2995/009; B29K 2105/00

See application file for complete search history.

(56) References Cited

U.S. PATENT DOCUMENTS

| | | |
|---|---|---|
| 4,902,724 A | 2/1990 | Moore |
| 5,322,861 A | 6/1994 | Tsuge et al. |
| 5,470,932 A | 11/1995 | Jinkerson |
| 5,556,929 A | 9/1996 | Yokoyama et al. |
| 5,616,630 A | 4/1997 | Heinze |
| 5,725,576 A | 3/1998 | Fedorov et al. |
| 5,880,171 A | 3/1999 | Lim et al. |
| 5,912,381 A | 6/1999 | Narayan et al. |
| 6,146,002 A | 11/2000 | Danapilis et al. |
| 6,200,732 B1 | 3/2001 | Tamura et al. |
| 6,201,036 B1 | 3/2001 | Fedorov et al. |
| 6,306,203 B1 | 10/2001 | Malhotra et al. |
| 6,353,069 B1 | 3/2002 | Freeman et al. |
| 7,132,492 B2 | 11/2006 | Lai et al. |
| 7,803,359 B1 | 9/2010 | Jinkerson et al. |
| 9,029,433 B2 | 5/2015 | Huang et al. |
| 9,365,501 B2 | 6/2016 | Tamura et al. |
| 2003/0162110 A1 | 8/2003 | Sacripante et al. |
| 2004/0056371 A1 | 3/2004 | Liao et al. |
| 2004/0266941 A1* | 12/2004 | Houston ............. C08F 290/046 524/506 |
| 2006/0293412 A1 | 12/2006 | Chou |
| 2009/0244479 A1 | 10/2009 | Zanini et al. |
| 2009/0248150 A1* | 10/2009 | Lehman .................... A61F 2/16 623/6.6 |

(Continued)

FOREIGN PATENT DOCUMENTS

| | | |
|---|---|---|
| EP | 1785747 A1 | 5/2007 |
| EP | 1785747 A1 | 5/2007 |

(Continued)

OTHER PUBLICATIONS

Definition of "consistency" from Merriam-Webster Dictionary (https://www.merriam-webster.com/dictionary/consistency).*

*Primary Examiner* — Christopher T Schatz
*Assistant Examiner* — Cynthia L Schaller
(74) *Attorney, Agent, or Firm* — Gokalp Bayramoglu

(57) ABSTRACT

This invention relates to a formulation and the lens manufacturing process in the areas of medicine, ophthalmology, cataracts and cataract surgery for the production of mainly intraocular lens (IOL) which is flexible, biocompatible and has long-shelf life.

8 Claims, No Drawings

(56) References Cited

U.S. PATENT DOCUMENTS

| | | |
|---|---|---|
| 2010/0113641 A1 | 5/2010 | Laredo |
| 2010/0140450 A1 | 6/2010 | Duret |
| 2010/0280144 A1 | 11/2010 | Kim et al. |
| 2012/0035292 A1* | 2/2012 | Onclin .................. C08F 2/50 522/79 |
| 2012/0232648 A1 | 9/2012 | Kahook et al. |
| 2013/0107201 A1 | 5/2013 | Argal et al. |
| 2013/0168617 A1* | 7/2013 | Alli .................. C08G 77/442 252/589 |
| 2015/0094393 A1* | 4/2015 | Holland ................ C08L 83/04 522/66 |

FOREIGN PATENT DOCUMENTS

| | | |
|---|---|---|
| EP | 2417929 A2 | 2/2012 |
| JP | 10282302 | 10/1998 |
| JP | 10282302 A | 10/1998 |
| RU | 2129880 B1 | 5/1999 |
| RU | 2132662 B1 | 7/1999 |
| RU | 2198630 B1 | 2/2003 |
| RU | 2198661 B1 | 2/2003 |
| RU | 2234417 B1 | 8/2004 |
| RU | 2239391 B1 | 11/2004 |
| RU | 2242189 B1 | 12/2004 |
| RU | 2275884 B1 | 5/2006 |
| RU | 2288494 B1 | 6/2006 |
| RU | 2309781 B1 | 11/2007 |
| RU | 2487726 B1 | 7/2013 |
| RU | 2521194 B1 | 6/2014 |
| RU | 2526182 B1 | 8/2014 |
| WO | WO9727223 A1 | 7/1997 |
| WO | WO-2007111973 A1 | 10/2007 |
| WO | WO-2011163126 A1 | 12/2011 |
| WO | WO-2012166948 A1 | 12/2012 |

* cited by examiner

US 10,351,637 B2

FORMULATION AND LENS MANUFACTURING PROCESS FOR THE PRODUCTION OF INTRAOCULAR LENS (IOL)

TECHNICAL FIELD

This invention relates to a formulation and the lens manufacturing process in the areas of medicine, ophthalmology, cataracts and cataract surgery for the production of mainly intraocular lens (IOL) which is flexible, biocompatible and has long-shelf life.

BACKGROUND

Natural intraocular lenses in the human eye lose its vision due to the build up problem on the surface of the lenses or damage of lenses by aging and/or diseases passed. Today, the build up problem on natural lenses replaced with the new synthetic lenses by an operation known as cataract surgery. Domestic natural eye lens in the human eye has been first replaced in 1949 using methyl methacrylate-based hard polymeric lens. In general, different acrylate lenses are used for this aim.

In recent years, surgeons prefer to use lenses with high reactive index, biocompatible, foldable intraocular lenses providing ease on micro incisional surgery.

Intraocular lens manufacturing technology is generally based on thermal polymerization method using a mold and forming it into the lens by turning machine coupled with laser technology. However, this method is time consuming and expensive and has dimensional stability problems due to the production method used. Moreover, invisible fractures can be encountered on the lens of the surface causing so-called glistening problems due to the use of turning processes.

Another manufacturing method for the production of intraocular lenses is the photopolymerization process which is an environmentally friendly and energy saving method. Said method is an appropriate method in terms of production costs. In the prior United States patent document No. U.S. Pat. No. 6,201,036 it is mentioned that an intraocular lens production obtained by the use of photopolymerization method.

In recent years, blue light (400-500 nm) were determined to pose a potential hazard to the retina. In the United States patent document No. U.S. Pat. No. 6,353,069 the production of lenses with high refractive index using two or more acrylate and/or methacrylate-containing copolymers in aromatic structure was mentioned. In the United State patent document of. No. U.S. Pat. No. 5,470,932 the addition of yellow paint into the formulation was mentioned. However, such nonreactive input like acrylate causes diffusion problems causing reduction of the activity of the ingredient by time.

UV (ultraviolet) blocking process as mentioned in Japanese Patent JP10282302 and European Patent No. EP1785747 and WO97/27223 can also be obtained by surface coating of the lenses. However, the desired results cannot be obtained in case of nonhomogeneous coatings. Lenses with non-blocking feature in the range of 300-430 nm may cause second cataract formation and cause negative results from the biocompatibility tests which is the indication of the long-term use results of the lenses.

"The AcrySof Natural Lens SN60AT" yellow lens produced by ALCON company has UV-blocking feature in the spectral transmittance values of 400-475 nm. It was believed and also observed during the eye transplantation operations that especially after 54 years old, natural lens are yellowing in order to reduce the damage of light in the 400-475 nm on retina. The body naturally adjusts itself to protect damage of light on this wave length. Researchers working on cataract surgery believed that this property should also be carried to the synthetic lenses for the patients at the age of 54 or older. ALCON company used ingredients that can absorb blue light and "AcrySof Natural" took commercial product on the market. In order to minimize the diffusion of the blue light absorbing ingredient from the lens ALCON added acrylic groups to the blue light absorbing ingredient as mentioned in the U.S. Pat. Nos. 5,470,932, 7,803,359 and US20100113641 numbered United States patent. All of the aforementioned lenses were obtained by molding thermally and shaping with turning coupled with laser.

United States patent No. US20120232648 mentioned lenses with a shape memory polymer (SMP) intraocular lens may have a refractive index above 1.45, a Tg between 10° C. and 60° C., inclusive, de minimis or an absence of glistening, and substantially 100% transmissivity of light in the visible spectrum. The intraocular lens is then rolled at a temperature above Tg of the SMP material. The intraocular device is radially compressed within a die to a diameter of less than or equal to 1.8 mm while maintaining the temperature above Tg. The compressed intraocular lens device may be inserted through an incision less than 2 mm wide in a cornea or sclera or other anatomical structure. The lens can be inserted into the capsular bag, the ciliary sulcus, or other cavity through the incision. The SMP can substantially achieve refractive index values of greater than or equal to 1.45.

In the United States patent document No. US20130107201, a multifocal ophthalmic device is disclosed, wherein the lens body comprises a curcuminoid compound as a UV-light stabilizer and/or co-polymeric composition which is drawn from pre-polymerization mixture of defined monomers lens body of the multifocal ophthalmic device is being formed. With a plurality of concentric annular Zones, which effect both diffraction and refraction of incident light, and which separated by slanted steps that are substantially devoid of any diffractive or refractive power.

SUMMARY

This invention relates to a formulation and the lens manufacturing process in the areas of medicine, ophthalmology, cataracts and cataract surgery for the production of mainly intraocular lens (IOL) which is flexible, biocompatible and has long-shelf life.

Another object of the invention is to realize a formulation and the intraocular lens manufacturing process providing an intraocular lens with UV-blocking property using a formulation containing reactive functional groups that can react at the region of 300-475 nm UV light.

Another object of the invention is to produce lenses using thermal and/or photopolymerization (UV/ultraviolet LED/light emitting device or UV/LED) and/or by combined use of both methods.

Another object of the invention is to provide an intraocular lens formulation and production method to obtain intraocular lenses with high refractive index.

Another object of the invention is to provide an intraocular lens formulation and production method for the production of a one piece hydrophobic intraocular lens.

Another object of the invention is to provide an intraocular lens formulation and production method by using photopolymerization process.

Another object of the invention is to provide an intraocular lens formulation and production method depending on the inputs and their ratios to obtain two different type of lenses with white or yellow color.

DETAILED DESCRIPTION

This invention relates to a formulation and the lens manufacturing process using photopolymerization which gives lenses with UV-blocking properties and smooth surface, flexible, high refractive index value, inexpensive, hydrophobic, and without glistening problem resulting from turning applications.

The formulation according to the present invention comprises:
20 to 80 percent by weight acrylate and/or methacrylate-based oligomer ingredients, used as binders in the formulation,
5 to 40 percent by weight acrylate and/or methacrylate based monomer ingredients, used as reactive diluents,
1 to 5 weight percent by weight acrylate and/or methacrylate based UV blocking ingredient(s), used as UV-blockers, and
0.1 to 5 percent by weight photoinitiator ingredient, used to initiate the photopolymerization process.

The oligomer used in the formulation according to the invention is between 20% to 80% and of the structure of urethane acrylate and/or urethane methacrylate based.

Monofunctional acrylate and/or methacrylate based reactive monomer in the formulation is in the range of 5% to 40% by weight and may be used in different structures like methacrylic acid, methyl carbitol methacrylate, phenoxyethyl methacrylate, octyl methacrylate, methyl methacrylate, hydroxyethyl methacrylate, ethoxyethyl methacrylate, ethyleneglycol dimethacrylate, N-vinyl pyrrolidone, allyl methacrylate, N,N-Dimethylacetamide, glyceryl methacrylate and tetraethylene glycol dimethacrylate.

UV blocking ingredient in the formulation is 1% to 5% by weight in the formulation. As UV blockers in the preferred embodiment of the invention; 2-(4-Benzoyl-3-hidrokisfenoks) ethyl acrylate), 4-Methacryloxy-2-hydroxybenzophenone), 2-(2'-Hydroxy-5'-methacryloxyethylphenyl)-2H-benzotriazole, coumarin or substances on the polyarylene ether structure is used.

The present invention formulation has photoinitiator to initiate the photopolymerization. The photoinitiator ratio in the formulation is 0.1% to 5% by weight and may be used in different structures like 2,4,6-trimetilbenzoildifenilfosf oxide, (2-benzyl-2-N-dimethylamino-1-(4-morpholinopropan-1), (hydroxycyclohexyl) phenyl ketone, 2-benzyl-2-N-dimethylamino-1-(4-morpholinopenil)-1-butanone, benzene, dimethyl ketal, isopropyl benzoin ketal, 2-n-propoxy-9H-9-thioxanthen-9-one and ethyl 4-(dimethylamino) benzoate.

Intra ocular lenses obtained by using the formulation of the invention give flexible and hydrophobic lenses with polymeric structure. Refractive index of the said lens is greater than or equal to 1.5. One piece (monobloc) lenses are produced in an economical manner without diffusion problems with photopolimerization method.

This invention relates to a formulation and the lens manufacturing process using photopolymerization process which gives lenses with smooth surface and UV-blocking properties, flexible, high refractive index value, inexpensive, and hydrophobic. All of the aforementioned lenses were obtained by molding thermally and shaping with turning coupled with laser. The method comprises the steps of:
  The preparation of the formulation,
  Placing the formulation into the die,
  Curing the formulation by photopolymerization method,
  Removing cured formulation from the die,
  Extraction with isopropyl alcohol and performing sterilization to the cured formulations.

In the method according to the present invention; a formulation is prepared by using between 20 to 80 by weight percent acrylate and/or methacrylate-based oligomer(s) as binders; between 5 to 40 weight percent acrylate and/or methacrylate-based monomers, as reactive diluent; between 0.1 to 5 weight percent photoinitiator to initiate the reaction; between 1 to 5 weight percent acrylate/or methacrylate-based UV blocker as UV absorbing ingredient. This formulation is transferred preferably into a quartz (quartz) die. The formulation contained in the die is cured by photopolymerization method. In a preferred embodiment of the invention for photopolymerization process, light sources are ultraviolet, LED or both ultraviolet and LED. The formulation (lens) was removed from the die after curing operation, extracted in isopropyl alcohol. Finally, the product is sanitized by subjecting to sterilization.

The intraocular lenses obtained in this invention have polymeric structures with flexible and hydrophobic properties. Refractive index of said lenses is greater than or equal to 1.5. Lenses are one piece (monobloc) which are produced in an economical manner without diffusion problems by photopolimerization method.

Around these fundamental concepts, the invention "Intraocular Lens Production provides a formulation and method" the development of related various applications are possible, the present invention is not limited to the examples described herein and is essentially according to the claims.

The invention claimed is:

1. A formulation, comprising:
  between 20 to 80 percent by weight acrylate and/or methylacrylate-based oligomer as a binder;
  between 5 to 40 percent by weight acrylate and/or methacrylate-based monomer as a reactive diluent, wherein the reactive diluent is one selected from the group consisting of methyl carbitol methacrylate and phenoxyethyl methacrylate;
  between 1 to 5 percent by weight acrylate and/or methacrylate-based UV blocker for absorbing light, wherein the UV blocker is one selected from the group consisting of 2-(4-Benzoyl-3-hydroxyphenoxy) ethyl acrylate, 2-(2'-Hydroxy-5'-methacryloxyethylphenyl)-2H-benzotriazole, and coumarin or polyaryl ether; and
  between 0.1 to 5 percent by weight photoinitiator to initiate the reaction, wherein the photoinitiator is one selected from the group consisting of (2-benzyl-2-N-dimethylamino-1-(4-morpholinopropan-1), 2-benzyl-2-N-dimethylamino-1-(4-morpholinopenil)-1-butanone, benzene, isopropyl benzoin ketal, 2-n-propoxy-9H-thioxanthen-9-one, and ethyl 4-(dimethylamino) benzoate.

2. The formulation according to claim 1, wherein the acrylate and/or methacrylate-based oligomer used in the formulation is a urethane acrylate-based oligomer.

3. The formulation according to claim 1, wherein the acrylate and/or methacrylate-based oligomer used in the formulation is a urethane methacrylate oligomer.

4. A method for manufacturing intraocular-use lenses by photopolymerization, comprising the following steps:

preparing a formulation,
placing the formulation into a die,
curing the formulation by a photopolymerization method to obtain a cured formulation,
removing the cured formulation from the die,
extracting the cured formulation with isopropyl alcohol and performing a sterilization on the cured formulation;
wherein the formulation is prepared by using between 20 to 80 by weight percent acrylate and/or methacrylate-based oligomer(s) as binders; between 5 to 40 weight percent acrylate and/or methacrylate-based monomers, as a reactive diluent; between 0.1 to 5 weight percent photoinitiator to initiate the reaction; and between 1 to 5 weight percent acrylate/or methacrylate-based UV blocker as UV absorbing ingredient;
wherein the reactive diluent is one selected from the group consisting of methyl carbitol methacrylate and phenoxyethyl methacrylate;
wherein the UV blocker is one selected from the group consisting of 2-(4-Benzoyl-3-hydroxyphenoxy) ethyl acrylate, 2-(2'-Hydroxy-5'-methacryloxyethylphenyl)-2H-benzotriazole, and coumarin or polyaryl ether;
wherein the photoinitiator is one selected from the group consisting of (2-benzyl-2-N-dimethylamino-1-(4-morpholinopropan-1), 2-benzyl-2-N-dimethylamino-1-(4-morpholinopenil)-1-butanone, benzene, isopropyl benzoin ketal, 2-n-propoxy-9H-thioxanthen-9-one, and ethyl 4-(dimethylamino) benzoate.

5. The method of claim 4, wherein the die is a quartz die.

6. The method of claim 4, wherein an LED and/or an Ultraviolet LED are used in the step of curing the formulation by the photopolymerization method.

7. The formulation according to claim 1, wherein the binder is between 60%-80% by weight, the acrylate and/or methacrylate-based UV blocker for absorbing light is between 1%-4% by weight, and the photoinitiator is 1%-5% by weight.

8. A formulation, consisting of:
between 20 to 80 percent by weight acrylate and/or methacrylate-based oligomer as a binder;
between 5 to 40 percent by weight acrylate and/or methacrylate-based monomer as a reactive diluent, wherein the reactive diluent is one selected from the group consisting of methyl carbitol methacrylate and phenoxyethyl methacrylate;
between 1 to 5 percent by weight acrylate and/or methacrylate-based UV blocker for absorbing light, wherein the UV blocker is one selected from the group consisting of 2-(4-Benzoyl-3-hydroxyphenoxy) ethyl acrylate, 2-(2'-Hydroxy-5'-methacryloxyethylphenyl)-2H-benzotriazole, and coumarin or polyaryl ether; and
between 0.1 to 5 percent by weight photoinitiator to initiate the reaction, wherein the photoinitiator is one selected from the group consisting of (2-benzyl-2-N-dimethylamino-1-(4-morpholinopropan-1), 2-benzyl-2-N-dimethylamino-1-(4-morpholinopenil)-1-butanone, benzene, isopropyl benzoin ketal, 2-n-propoxy-9H-thioxanthen-9-one, and ethyl 4-(dimethylamino) benzoate.

* * * * *